United States Patent
Moore et al.

(10) Patent No.: US 10,334,847 B2
(45) Date of Patent: Jul. 2, 2019

(54) ANTIFUNGAL COMPOSITION (71) Applicant: The University of Sussex, Brighton (GB)

(72) Inventors: Anthony Moore, Brighton (GB); Luke Young, Brighton (GB); Benjamin May, Brighton (GB)

(73) Assignee: THE UNIVERSITY OF SUSSEX

( * ) Notice: Subject to any disclaimer, the term of this patent is extended or adjusted under 35 U.S.C. 154(b) by 0 days.

(21) Appl. No.: 15/113,046

(22) PCT Filed: Jan. 23, 2015

(86) PCT No.: PCT/GB2015/050148
§ 371 (c)(1),
(2) Date: Jul. 20, 2016

(87) PCT Pub. No.: WO2015/110820
PCT Pub. Date: Jul. 30, 2015

(65) Prior Publication Data
US 2017/0006864 A1    Jan. 12, 2017

(30) Foreign Application Priority Data
Jan. 23, 2014   (GB) .................................. 1401117.5

(51) Int. Cl.
| *A01N 35/04* | (2006.01) |
| *A01N 37/46* | (2006.01) |
| *A01N 43/40* | (2006.01) |
| *A01N 43/54* | (2006.01) |
| *A01N 43/653* | (2006.01) |
| *A01N 47/24* | (2006.01) |
| *A01N 47/38* | (2006.01) |
| *A01N 59/20* | (2006.01) |
| *A61K 31/11* | (2006.01) |
| *A61K 31/216* | (2006.01) |
| *A61K 31/415* | (2006.01) |
| *A61K 31/4152* | (2006.01) |
| *A61K 31/4196* | (2006.01) |
| *A61K 31/44* | (2006.01) |
| *A61K 31/505* | (2006.01) |
| *A61K 33/34* | (2006.01) |

(52) U.S. Cl.
CPC ............ *A01N 35/04* (2013.01); *A01N 37/46* (2013.01); *A01N 43/40* (2013.01); *A01N 43/54* (2013.01); *A01N 43/653* (2013.01); *A01N 47/24* (2013.01); *A01N 47/38* (2013.01); *A01N 59/20* (2013.01); *A61K 31/11* (2013.01); *A61K 31/216* (2013.01); *A61K 31/415* (2013.01); *A61K 31/4152* (2013.01); *A61K 31/4196* (2013.01); *A61K 31/44* (2013.01); *A61K 31/505* (2013.01); *A61K 33/34* (2013.01)

(58) Field of Classification Search
None
See application file for complete search history.

(56) References Cited

U.S. PATENT DOCUMENTS

| 4,225,619 A * | 9/1980 | Brickl ................... A01N 35/04 514/520 |
| 2007/0142410 A1* | 6/2007 | Garnier .................. A01N 33/12 514/269 |

FOREIGN PATENT DOCUMENTS

| GB | 2511470 A | 8/2012 | |
| JP | H06245778 A | 6/1994 | |
| JP | 2008/056602 A | 3/2008 | |
| JP | 2013/507372 A | 3/2013 | |
| WO | WO 2011/044213 A1 | 4/2011 | |
| WO | WO 13/160670 A1 | 10/2013 | |
| WO | WO 2013/160670 | * 10/2013 | ............. C07C 39/24 |
| WO | WO 15/110820 A1 | 7/2015 | |

OTHER PUBLICATIONS

Gutierrez et al., J. Agric. Food Chem., 2005, 53(20), pp. 7701-7708.*

Gutierrez et al., "Bioactive Metabolites from the Fungus *Nectria gelligena*, the Main Apple Canker Agent in Chile," J. Agric. Food Chem., 53(20):7701-7708, , doi: 10.1021/jf0510211, (2005).

Hussain et al., "Antimicrobial constituents from endophytic fungus *Fusarium* sp," Asian Pacific Journal of Tropical Disease, 5(3):186-189, doi: 10.1016/S2222-1808(14)60650-2, (2015). Available online Jul. 29, 2014.

WIPO Application No. PCT/GB2015/050148, PCT International Preliminary Report on Patentability dated Jul. 26, 2016.

WIPO Application No. PCT/GB2015/050148, PCT International Search Report dated Feb. 25, 2015.

WIPO Application No. PCT/GB2015/050148, PCT Written Opinion of the International Searching Authority dated Feb. 25, 2015.

* cited by examiner

*Primary Examiner* — Brian Gulledge
(74) *Attorney, Agent, or Firm* — Alston & Bird LLP (57) ABSTRACT

The present invention provides antifungal compositions, and in particular, to antifungal formulations comprising a combination of an antifungal active agent and an AOX inhibitor for use in treating fungal infections in plants and animals.

14 Claims, 3 Drawing Sheets

ANTIFUNGAL COMPOSITION

CROSS REFERENCE TO RELATED APPLICATIONS

This application is a US national stage of PCT/GB2015/050148 filed Jan. 23, 2015, incorporated by reference, which claims the benefit of GB 1401117.5 filed Jan. 23, 2014.

The present invention relates to antifungal compositions, and in particular, to antifungal formulations comprising a combination of antifungal active agents for use in treating fungal infections in plants and animals.

Mitochondria are the power-house of the cell and, therefore, inhibition of the processes that result in an organism's energy conservation have a major impact on their capability to survive. The most successful class of agricultural fungicides are therefore a set of specific inhibitors which specifically target the mitochondrial respiratory chain. Inhibitors known as strobilurins, which target the oxidation of ubiquinol, a pivotal respiratory chain component, have improved the standards of disease control in plants. Strobilurins inhibit fungal respiration and, hence, ATP synthesis by binding to the ubiquinol binding site of Complex III (the $bc_1$ complex), which is essential for fungal respiration.

WO 2013/160670 discloses a range of different compounds for use in inhibiting microbial alternative oxidase (AOX) and/or cytochrome $bc_1$ complex. One of the compounds disclosed in WO 2013/160670 (i.e. Colletochlorin B) was shown to have particularly effective inhibition of AOX and cytochrome $bc_1$ complex. However, in spite of the efficacy of the antifungal compounds described in WO 2013/160670, there continues to be an ongoing need for more potent antifungal compositions, for use in either agrochemicals or anti-parasitic pharmaceuticals for treating fungal infections in animals.

The inventors therefore prepared a series of novel formulations comprising several of the compounds described in WO 2013/160670 in combination with a number of different fungicides, and tested the resultant antifungal activities. They were surprised to observe a synergistic effect between the two compounds in each combined formulation.

Thus, according to a first aspect of the invention, there is provided an antifungal composition comprising an antifungal agent and a compound of formula I:—

[Formula I]

wherein $R^1$ is selected from a nitrile group, an alkyl, alkenyl, amine, alkoxy, aldehyde, ketone, carboxylic acid, ester and amide group with 1 to 4 C-atoms that is optionally mono- or polysubstituted by F, O, $NH_2$ or CN, and in which one or more non-adjacent $CH_2$ groups are optionally replaced, in each case independently from one another, by —O—, —NH—, —CO—, —COO—, or —OCO—;

$R^2$ is hydrogen or a hydroxy or alkoxy group with 1 to 3 C atoms;

$R^3$ is a straight chain or branched alkyl or alkylene with 4 to 20 C atoms, that is optionally mono- or polysubstituted by a $C_1$ to $C_4$ alkyl group;

$R^4$ is hydrogen or a hydroxy or alkoxy group with 1 to 3 C atoms;

$R^5$ is a halogen group; and $R^6$ is H or a $C_1$ to $C_4$ alkyl group;

with the proviso that at least one of $R^2$ and $R^4$ is a hydroxy or alkoxy group with 1 to 3 C atoms.

The antifungal agent may be selected from a group of antifungal agents consisting of: a member of the phenylamide fungicide family; a member of the strobilurin family; a DeMethylation Inhibitor; $CuPC_{33}$; Boscalid; Difenconcozole; and Pyraclostrobin.

Preferably, the member of the phenylamide fungicide family is Metalaxyl. Thus, in a preferred embodiment, the composition comprises Metalaxyl and the compound (I), as defined herein.

Preferably, the member of the strobilurin family is Azoxystrobin. Thus, in another preferred embodiment, the composition comprises Azoxystrobin and the compound (I), as defined herein.

It will be appreciated that the compound of formula I is preferably an inhibitor of AOX and/or cytochrome $bc_1$ complex. Where any group of compound (I) is an alkyl group, it may be a $C_1$, $C_2$, $C_3$ or $C_4$ alkyl, for example a methyl, ethyl, propyl or butyl group. Optionally, the alkyl group may be substituted with one or more heteroatoms, for example nitrogen, oxygen, sulphur, phosphorous or a halogen.

$R^1$ may be a group selected from: CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$.

$R^2$ may be a short-chain alkyl, for example a methyl, ethyl or propyl group. However, preferably $R^2$ is a hydroxyl group.

$R^3$ may be a straight chain or branched alkyl or alkylene with 6 to 15 C atoms, 8 to 12 C atoms or 8 to 10 C atoms, that is optionally mono- or polysubstituted by a $C_1$ to $C_4$ alkyl group. For example, $R^3$ may be branched diene having 6 to 15 C atoms that is substituted with at least one, and preferably two, methyl groups.

$R^4$ may be a methyl, ethyl or propyl group. However, preferably $R^4$ is a hydroxyl group.

$R^5$ may be a chlorine, bromine, fluorine or iodine group. Preferably, $R^5$ is a chlorine group.

$R^6$ may be a methyl, ethyl or propyl group. However, preferably $R^6$ is a methyl group.

In one embodiment of compound of formula I:—

$R^1$ is selected from CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$; and wherein $R^2$ is a hydroxyl group;

$R^3$ is a straight chain or branched alkyl or alkylene with 4 to 20 C atoms, that is optionally mono- or polysubstituted by a $C_1$ to $C_4$ alkyl group;

$R^4$ is a hydroxyl group;

$R^5$ is a chlorine atom; and $R^6$ is H or a $C_1$ to $C_4$ alkyl group.

In another embodiment of a compound of formula I:—

$R^1$ is selected from CHO; $CH_2OH$; CN; $CH_3$; $C(O)NH_2$; $C(O)NHCH_3$; $C(O)CH_3$; $CF_2CH_3$; $CH_2CH_3$; $CH_2OAc$; COOH; and $COOCH_3$; and wherein $R^2$ is a hydroxyl group;

$R^3$ is a straight chain or branched alkyl or alkylene with 6 to 15 C atoms, that is optionally mono- or polysubstituted by a $C_1$ to $C_2$ alkyl group;

$R^4$ is a hydroxyl group;
$R^5$ is a chlorine atom; and
$R^6$ is H or a $C_1$ to $C_4$ alkyl group.

In one preferred embodiment of compound of formula I:—
$R^1$ is selected from CHO; $CH_2OH$; CN; $CH_3$; $C(O)NH_2$; $C(O)NHCH_3$; $C(O)CH_3$; $CF_2CH_3$;
$CH_2CH_3$; $CH_2OAc$; COOH; and $COOCH_3$; and wherein
$R^2$ is a hydroxyl group;
$R^3$ is an alkylene chain having 8 to 10 C atoms, and is substituted with at least one methyl group, preferably two methyl groups;
$R^4$ is a hydroxyl group;
$R^5$ is a chlorine atom; and
$R^6$ is a methyl group.

Figure 1:
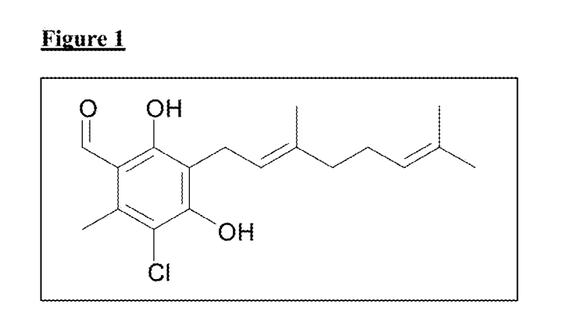
FIG. 1 represents the chemical formula of one embodiment of compound I used in the composition of the invention, i.e. Colletochlorin B.
Figure 2:
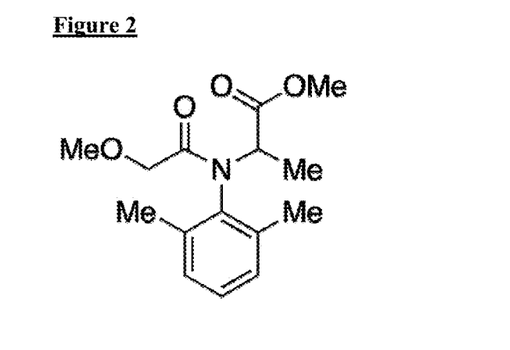
FIG. 2 represents the chemical formula of Metalaxyl.
Figure 3:
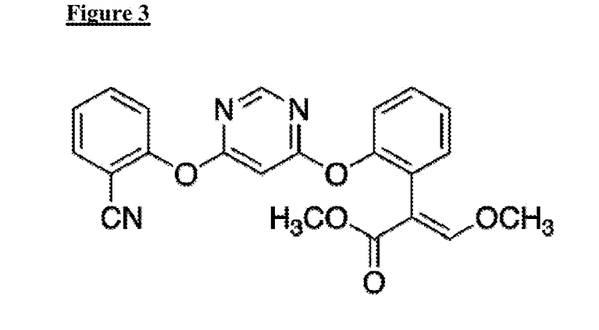
FIG. 3 represents the chemical formula of Azoxystrobin.
Figure 4:
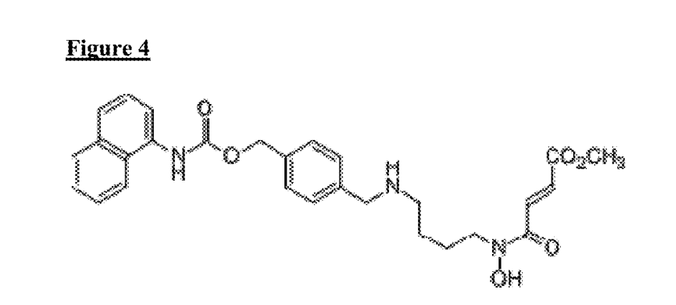
FIG. 4 represents the chemical formula of one embodiment of a DeMethylation Inhibitor (DMI)
Figure 5:
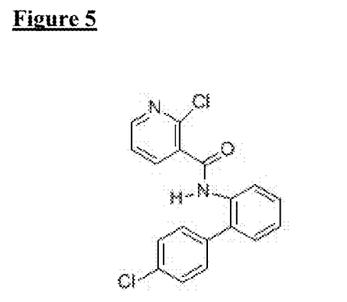
FIG. 5 represents the chemical formula of Boscalid.
Figure 6:
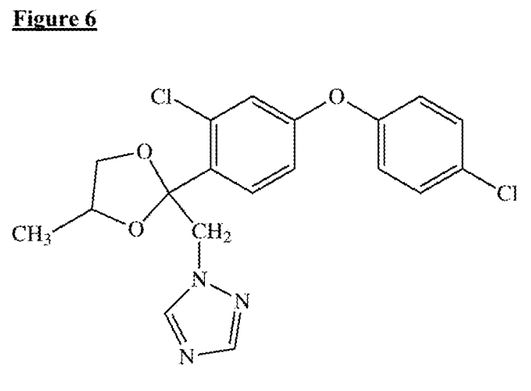
FIG. 6 represents the chemical formula of Difenconcozole.

Preferably, in compound of formula I:—
$R^1$ is CHO;
$R^2$ is a hydroxyl group;
$R^3$ is an alkylene chain having 8 to 10 C atoms, and is substituted with at least one methyl group, preferably two methyl groups;
$R^4$ is a hydroxyl group;
$R^5$ is a chlorine atom; and
$R^6$ is a methyl group. It will be appreciated that this compound of formula I is known as Colletochlorin B, which is represented in FIG. 1.

In some preferred embodiments, $R^1$ is not a CHO group.

Preferably, the antifungal composition comprises 0.1-20 μm, 0.5-15 μm or 1-10 μM, of the antifungal agent.

Preferably, the antifungal composition comprises 0.1-10 μM, 0.5-5 μM or 0.8-2 μM, of the compound of formula I, which is most preferably Colletochlorin B.

The antifungal composition of the first aspect comprising the antifungal agent and compound of formula I is preferably an agrochemical.

Thus, in a second aspect, there is provided an agrochemical composition comprising the antifungal composition according to the first aspect.

In a third aspect, there is provided use of the antifungal composition according to the first aspect, as an agrochemical.

In a fourth aspect, there is provided a method of treating, ameliorating or preventing an agrochemical disease or infection in a plant, the method comprising contacting a plant in need of such treatment with agrochemically effective amounts of an antifungal agent and a compound of formula I.

The use of the third aspect or the method of the fourth aspect preferably comprises contacting the plant with an agrochemically effective amount of the composition of the first aspect.

An agrochemical disease, which may be treated by the method of the fourth aspect, may be caused by an organism selected from a group of organisms consisting of: *Chalara fraxinea*; *Septoria tritici*; *Gaeumannomyces graminis* var *titici*; *Magnaporthe grisea*; *Magnaporthe oryzae*; *Rhizoctonia solani*; *Botrytis cinerea*; *Fusicladium effusum* syn. *Cladosporium caryigenum* and *Fusicladosporium effusum*; *Carya illinoinensis*; *Podosphaera fusca*; *Microdochium nivale*; *Microdochium majus*; *Septoria nodoum*; *Tapesia acuformis*; *Mycosphaerella fijiensis*; and *Metarhizium anisopliae*.

It will be appreciated that each of the organisms referred to herein will have an AOX.

It will be appreciated that *Septoria tritici* and *Gaeumannomyces graminis* var *titici* are wheat pathogens (take-all); *Magnaporthe grisea* and *Magnaporthe oryzae* may cause rice blast and grey leaf spot of rye grass; *Rhizoctonia solani* may cause black scurf of potato, *Botrytis cinerea* may cause grey mold—a necrotrophic fungus that affects many plant species, although its most notable hosts are wine grapes; *Fusicladium effusum* (syn. *Cladosporium caryigenum* and *Fusicladosporium effusum* is known as the Pecan scab and is the most devastating disease of the commercial pecan; *Carya illinoinensis* is involved in the production in South Eastern United States; *Podosphaera fusca* is the main causal agent of cucurbit powdery mildew in Spain and one of the most important limiting factors for cucurbit production worldwide; *Microdochium nivale* & *majus* may attack barley, durum wheat and soft wheat and is present in all areas of France; *Septoria nodoum* may cause leaf and glume blotch; and *Tapesia acuformis* may cause eyespot. *Mycosphaerella fijiensis* causes the banana fungal disease Black Sigatoka (black leaf streak). In addition, there is growing agrochemical interest in *Metarhizium anisopliae* which is an entomopathogenic fungus as an alternative for the management of pest insects.

It will be appreciated that *Chalara fraxinea* causes *Chalara* ash dieback disease.

The agrochemical composition of the second aspect may comprise one or more solvents in which the antifungal agent and compound of formula I is mixed. The amount of solvents in the composition may range from 1% to 99%, or from 30% to 80%. Suitable solvents include, for example, a non-polar water-immiscible solvent, or a polar aprotic water miscible organic solvent. Non-polar solvents include, for example substituted or unsubstituted aliphatic or aromatic hydrocarbons and esters of plant oils or mixtures thereof. Non-limiting examples of aromatic hydrocarbons include benzene or substituted benzene derivatives such as toluene, xylene, 1,2,4-trimethylbenzene, naphthalene or mixtures thereof. In one embodiment, a solvent includes a mixture of napthalen and 1,2,4-trimethylbenzene. In another embodiment, a solvent is Aromatic 150, a heavy aromatic naptha solvent containing <10% naphthalene and <1.7% 1,2,4-trimethylbenzene.

Alkyl esters can also be used as non-polar, water immiscible solvents. Plant oils may be esterified with various alcohols to form alkyl esters of plant oils. Fatty acids of these plant oils have 5 to 20, or 6 to 15 carbon atoms. Alkyl esters of plant oils include, without limitation, methyl, ethyl and butyl esters of canola (*B. napus*), linseed, safflower (Carthamus tinctorius L), soybean and sunflower oils. In one embodiment, the solvent is a mixture of methyl esters. A specific non-limiting example of methyl esters is Agent 2416-21 manufactured by Stepan Company (22 W. Frontage Road, Northfield, Ill.).

Water-miscible polar aprotic solvents can include, for example, alkyl lactates, isopropyl lactate, alkyl carbonates, polyethylene glycols, polyethylene glycol alkyl ethers, polypropylene glycols, and polypropylene glycol alkyl ethers, or mixtures thereof.

The agrochemical composition of the second aspect may comprise one or more adjuvants. An adjuvant may enhance or improve herbicidal performance, for example. Adjuvants may be added to the composition at the time of formulation, or by the applicator to a mix prior to treatment. Adjuvants include, for example surfactants (emulsifier), crop oil, fertilizers, dispersing agents, compatibility agents, foaming activators, foam suppressants, correctives, and spray colorants (dyes). An adjuvant may be present in any desired amount. For example, a formulation may contain 1% to 3% adjuvant, 3% to 8% of adjuvant, 8% to 16% adjuvant, 17% to 30% adjuvant, or 30% or (e.g. 40% or more) more adjuvant.

The agrochemical composition may comprise one or more surfactant. A surfactant may increase solubility of the antifungal agent and compound of formula I in a solution. A surfactant may also affect spray retention, droplet spreading, and dry rates. A surfactant may be anionic or non-ionic. Examples of anionic surfactants include phosphoric mono- and di-esters of long-chain alcohols having 14 to 22 carbon atoms and the salts thereof; phosphoric mono- and di-esters of alkylene oxide addition products of long-chain alcohols having 14 to 22 carbon atoms and the salts thereof; alkyl-sulphates having 14 to 22 carbon atoms; polyoxyethylene alkyl ether sulphates of alcohols having 14 to 22 carbon atoms; alkane sulphonates having 14 to 22 carbon atoms; and olefin sulphonates having 14 to 22 carbon atoms.

Suitable non-ionic surfactants include, for example, ethoxylated fatty acids, alcohol ethoxylates, tristyrylphenol ethoxylates, ethoxylated sorbitan fatty acid esters or mixtures thereof. Ethoxylated fatty acids include castor or canola oil ethoxylates having at least 25, preferably 27 to 37 ethoxy units, such as Sunaptol® CA350 (castor oil ethoxylate with 35 ethoxy units) of Uniqema (formerly ICI Surfactants), Mergital® EL33 (castor oil ethoxylate with 33 ethoxy units) of Henkel KGaA, Eumulgin® Co3373 (canola oil ethoxylate with 30 ethoxy units) of Henkel KGaA and Ukanil® 2507 (castor oil ethoxylate) of Uniqema.

Surfactants may be present in any desired amount. For example, a surfactant may be present in an amount of about 0.1 to about 30% by weight in the formulation. In a particular embodiment, a surfactant is present in an amount of about 1 to about 9% by weight in the formulation. In another embodiment, a surfactant is present in an amount of about 10 to about 20% by weight in the formulation.

The agrochemical composition may comprise one or more emulsifier. An emulsifier is a type of surfactant typically used to keep emulsion well-dispersed. Non-limiting examples of the emulsifier include Agent 2201-76, Agent 2416-20, Emulpon CO-360, T-Det C-40®, and Agnique™ SBO-IO. Agent 2201-76 is manufactured by Stepan Company (22 W. Frontage Road, Northfield, Ill.), which is a blend of nonionic and anionic surfactants (82%). The ingredients in Agent 2201-76 are alkylbenzene sulfonate and fatty acid ethoxylate, aromatic petroleum hydrocarbon, 1-hexanol and naphthalene. Agent 2416-20 is also manufactured by Stepan Company (22 W. Frontage Road, Northfield, Ill.), which is a blend of nonionic and anionic surfactants (35-37%). Agent 2416-20 also includes aromatic petroleum hydrocarbon (57-58%), and naphthalene (6-7%). Emulpon CO-360 is manufactured by Akzo Nobel Chemicals Ltd. (525 West Van Buren, Chicago, Ill.), which contains ethoxylated castor oil (100% by weight) and oxirane (<0.001% by weight). T-Det C-40® may be purchased from Harcros Organics (5200 Speaker Road., P.O. Box 2930, Kansas City, Kans.), or from Akzo Nobel Chemicals Ltd. (525 West Van Buren, Chicago, Ill.), which is a non-ionic emulsifier, and a brand of ethoxylated (polyethoxylated) castor oil. Agnique™ SBO-IO is manufactured by Cognix GmbH headquartered in Monheim, Germany, which contains alkoxylated triglycerides as an ethoxylated soybean oil.

A crop oil, or a crop oil concentrate, may be used to increase the efficacy of a herbicide formulation. Although not wishing to be bound by any particular theory, a crop oil is believed to keep the leaf surface moist longer than water, which in turn allows more time for the herbicide to penetrate, thereby increasing the amount of herbicide that will enter the plant (e.g. weed). A crop oil can improve uptake of herbicide by plant (e.g. weed). A crop oil can therefore improve, enhance, increase or promote herbicidal efficacy or activity. Crop oils may contained from 1% to 40% by weight, or 1% to 20% by weight in the formulation. A crop oil can be derived from either petroleum oil or vegetable oil. Non-limiting examples of crop oil include soybean oils and petroleum based oils.

The agrochemical composition of the invention may be in customary formulations. Non-limiting examples include solutions, emulsions, suspensions, wettable powders, powders, dusts, pastes, soluble powders, granules, pellets, emulsifiable concentrate, oil spray, aerosol, natural and synthetic materials impregnated with active compound, and very fine capsules (e.g. in polymeric substances). In certain embodiments, the composition is in a form of an emulsifiable concentrate, wettable powder, granule, dust, oil spray or aerosol.

The agrochemical composition may optionally include adherent coatings. Such coatings include those that aid the antifungal agent and compound of formula I to adhere to the intended environment, for example, a plant being treated. Adherent coatings include carboxymethylcellulose, natural and synthetic polymers in various forms, such as powders, granules or latexes. Other adherent coatings include gum arabic, polyvinyl alcohol and polyvinyl acetate. Phospholipids, such as cephalins and lecithins, and synthetic phospholipids are also examples of adherent coatings. Further additives may be mineral and vegetable oils.

Colourants can also be included in the agrochemical composition. Non-limiting examples are inorganic pigments, such as iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The agrochemical composition according to the invention can be applied in the form of ready mixes. Herbicidal compositions can also be formulated individually and mixed upon use, i.e. applied in the form of tank mixes. The compositions of the invention can be used as such or in the form of their formulations, and furthermore also as mixtures with herbicides, ready mixes or tank mixes. The compositions may also be mixed with other active compounds, such as other fungicides, insecticides, acaricides, nematicides, bird repellents, growth substances, plant nutrients and agents which improve soil structure. For particular application purposes, in particular when applied post-emergence, formulations such as mineral or vegetable oils which are tolerated by plants (for example the commercial product "Oleo DuPont 1 IE") or ammonium salts such as, for example, ammonium sulphate or ammonium thiocyanate, as further additives can be included.

The compositions can be used as such, in the form of their formulations or in the forms prepared therefrom by dilution of a concentrated form, such as ready-to-use or concentrated liquids, solutions, suspensions, emulsions, or solids, such as, powders, pastes, granules and pellets. They are dispersed in the customary manner, for example by watering, spraying, atomizing, dusting or scattering.

The compositions of the invention can be produced by mixing or suspending one or more stabilizers, an active ingredient, and optionally an adjuvant, a diluent or a solvent. In certain embodiments, compositions of the invention can be produced, for example by first mixing or suspending one or more antifungal agent and/or the compound of formula I with a diluent or solvent. Next, the appropriate amount of adjuvant is combined to the resulting mixture containing the antifungal agent and compound of formula I. The antifungal agent and compound of formula I can be added at the end and blended until the formulation becomes mostly or entirely homogeneous.

Plants that may be treated with the agrochemical composition are generally referred to herein as "crop plants". The term "crop plants" as used herein, includes any edible or non-edible plant, including decorative, plant species with commercial value, which is planted and cultivated for commercial use. Thus, crop plants include floral and non-floral plants, trees, vegetable plants, turf, and ground cover. Non-limiting specific examples of crop plants include canola, flax, peas, lentils, beans, linola, mustard, chickpeas, sunflowers, potatoes, seedling alfalfa, onions, soybeans and turf grass. The term "plants" is meant to include germinant seeds, emerging seedlings, and established vegetation, including roots and above-ground portions (for example, leaves, stalks, flowers, fruits, branches, limbs, root, etc.). The term "turf" used herein refers to grass which grow in areas in which they are desired, or purposely planned for and maintained, for example, a lawn. Turf also refers to a sod, where the surface layer of ground consisting of a mat of grass and grass roots.

The application rate of antifungal agent and compound of formula I varies depending, for example, on the crop being treated with the agrochemical composition. In general, the application rate may be from 0.01 kg/ha to 5.00 kg/ha or from 0.03 kg/ha to 3.00 kg/ha of the antifungal agent and/or compound of formula I.

The inventors have also found that the inhibitors of the invention can be effectively used to treat infections of animal or human fungal pathogens which comprise an AOX enzyme.

In a fifth aspect, therefore, there is provided the antifungal composition according to the first aspect, for use in therapy or as a medicament.

In a sixth aspect, there is provided the antifungal composition according to the first aspect, for use in treating a fungal infection.

In a seventh aspect, there is provided a method of treating, ameliorating or preventing a fungal infection in a subject, the method comprising, administering to a subject in need of such treatment, therapeutically effective amounts of an antifungal agent and a compound of formula I.

In an eighth aspect, there is provided a method of inhibiting activity of a microbial alternative oxidase (AOX) and/or cytochrome $bc_1$ complex, the method comprising contacting a microbial alternative oxidase (AOX) and/or cytochrome $bc_1$ complex with therapeutically effective amounts of an antifungal agent and a compound of formula I.

Preferably, the antifungal composition is used to treat any fungal infection. For example, fungi against which the composition is effective may include a filamentous fungus, such as an *Ascomycete*. Examples of fungi against which the composition is effective may be selected from a group of genera consisting of *Aspergillus; Blumeria; Candida; Cryptococcus; Encephalitozoon; Fusarium; Leptosphaeria; Magnaporthe; Phytophthora; Plasmopara; Pneumocystis; Pyricularia; Pythium; Puccinia; Rhizoctonia; richophyton*; and *Ustilago*.

Preferred examples of fungi may be selected from a group of genera consisting of *Aspergillus* and *Candida*. The fungus may be selected from a group of species consisting of *Aspergillus flavus; Aspergillus fumigatus; Aspergillus nidulans; Aspergillus niger; Aspergillus parasiticus; Aspergillus terreus; Blumeria graminis; Candida albicans; Candida cruzei; Candida glabrata; Candida parapsilosis; Candida tropicalis; Cryptococcus neoformans; Encephalitozoon cuniculi; Fusarium solani; Leptosphaerianodorum; Magnaporthe grisea; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Trichophytoninterdigitale; Trichophyton rubrum*; and *Ustilago maydis*.

As described in Example 2, a formulation comprising Colletochlorin B and azoxystrobin displayed surprisingly synergistic characteristics against the yeast, *S. cerevisiae* in which an AOX had been expressed.

Thus, further preferred examples of fungi include yeast, such as from the phylum ascomycota, or genus *Saccharomyces* spp., e.g. *S. cerevisiae*, or *Candida* spp, and *C. albicans*, which is known to infect humans.

The antifungal composition may be used to treat a disease associated with human pathogens, such as intestinal disease; Leishmaniasis; Candidiasis; and diseases associated with contact lens usage.

It will be appreciated that *Trypanosoma, Cryptosporidium parvum* and *Blastocystis hominis* can cause intestinal diseases; Leishmaniasis is caused by the *Leishmani* parasite; Candidiasis is caused by *Candida albicans* (commonly known as thrush); and diseases associated with contact lens usage may be caused by the free-living protozoan *Acanthamoeba*.

The antifungal agent and a compound of formula I may be administered contemporaneously (e.g. as a composition according to the first aspect of the invention) or sequentially. If administered sequentially, the antifungal agent and compound of formula I should be therapeutically active within the subject being treated at the same time.

Treating fungal diseases with antifungal agent and compound of formula I according to the invention is particularly useful because such therapy results in surprisingly synergistic actions. Furthermore, satisfactory therapy may be effected using lower doses than would be required in a monotherapy. This has the advantage that any deleterious side-effects associated with high doses of the antifungal agent and compound of formula I may be obviated or reduced.

The antifungal agent and compound of formula I may be used to treat existing medical conditions but may also be used when prophylactic treatment is considered medically necessary.

The antifungal agent and compound of formula I according to the invention may be combined in antifungal compositions having a number of different forms depending, in particular, on the manner in which the composition is to be used. Thus, for example, the antifungal composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the antifungal agent and compound of formula I may be used in a number of ways. For instance, oral administration may be required, in which case the antifungal agent and compound of formula I may be contained within a composition that may, for example, be ingested orally in the form of a tablet, capsule or liquid. Compositions comprising compounds of the invention may be administered by inhalation (e.g. intranasally). Compositions may also be formulated for topical use. For instance, gels, creams or ointments may be applied to the skin, for example, adjacent the treatment site, i.e. site of existing or potential fungal infection.

Antifungal agent and compounds of formula I may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with compounds used according to the invention is required and which would normally require frequent administration (e.g. at least daily injection).

In a preferred embodiment, antifungal agent and compound of formula I may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the antifungal agent and compound of formula I that is required is determined by their biological activity and bioavailability, which in turn depends on the mode of administration, the physiochemical properties of each compound and whether it is being used as a monotherapy or in a combined therapy. The frequency of administration will also be influenced by the half-life of the antifungal agent and compound of formula I within the subject being treated. Optimal dosages to be administered may be determined by those skilled in the art, and will vary with the particular compounds in use, the strength of the pharmaceutical composition, the mode of administration, and the advancement of the fungal infection being treated.

Additional factors depending on the particular subject being treated will result in a need to adjust dosages, including subject age, weight, gender, diet, and time of administration.

Generally, a daily dose of between 0.01 µg/kg of body weight and 0.5 g/kg of body weight of the antifungal agent and compound of formula I according to the invention may be used for treating, ameliorating, or preventing the microbial infection, depending upon which compound is used. More preferably, the daily dose of antifungal agent and compound of formula I is between 0.01 mg/kg of body weight and 500 mg/kg of body weight, more preferably between 0.1 mg/kg and 200 mg/kg body weight, and most preferably between approximately 1 mg/kg and 100 mg/kg body weight.

The antifungal agent and compound of formula I may be administered before, during or after onset of the microbial infection. Daily doses may be given as a single administration (e.g. a single daily injection). Alternatively, the antifungal agent and compound of formula I may require administration twice or more times during a day. As an example, antifungal agent and compound of formula I may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of compounds according to the invention to a patient without the need to administer repeated doses.

Known procedures, such as those conventionally employed by the pharmaceutical industry (e.g. in vivo experimentation, clinical trials, etc.), may be used to form specific formulations comprising the antifungal agent and compound of formula I according to the invention and precise therapeutic regimes (such as daily doses of the compounds and the frequency of administration). The inventors believe that they are the first to describe a composition for treating microbial infections, based on the combined use of the antifungal agent and compound of formula I.

Hence, in a ninth aspect of the invention, there is provided an antifungal pharmaceutical composition comprising an antifungal agent and a compound of formula I, and a pharmaceutically acceptable vehicle.

The invention also provides, in a tenth aspect, a process for making the antifungal pharmaceutical composition according to the ninth aspect, the process comprising contacting therapeutically effective amounts of an antifungal agent and a compound of formula I with a pharmaceutically acceptable vehicle.

The antifungal agent may be selected from a group of antifungal agents consisting of: a member of the phenylamide fungicide family; a member of the strobilurin family; a DeMethylation Inhibitor; CuPC33; Boscalid; Difenconcozole; and Pyraclostrobin.

Preferably, the member of the phenylamide fungicide family is Metalaxyl. Thus, in a preferred embodiment, the antimicrobial composition comprises Metalaxyl and the compound (I), as defined herein.

Preferably, the member of the strobilurin family is Azoxystrobin. Thus, in another preferred embodiment, the antimicrobial composition comprises Azoxystrobin and the compound (I), as defined herein.

Compound (I) is as defined herein.

A "subject" may be a vertebrate, mammal, or domestic animal. Hence, inhibitors, compositions and medicaments according to the invention may be used to treat any mammal, for example livestock (e.g. a horse), pets, or may be used in other veterinary applications. Most preferably, however, the subject is a human being.

A "therapeutically effective amount" of the antifungal agent and a compound of formula I is any amount which, when administered to a subject, is the amount of medicament or drug that is needed to treat the microbial infection, or produce the desired effect, i.e. inhibition of AOX and/or cytochrome $bc_1$ complex.

For example, the therapeutically effective amount of the antifungal agent and a compound of formula I may be from about 0.01 mg to about 800 mg, and preferably from about 0.01 mg to about 500 mg. It is preferred that the amount of the antifungal agent and a compound of formula I is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the antifungal agent and a compound of formula I) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The antifungal agent and a compound of formula I may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The active compound may be prepared as a sterile solid composition that may be dissolved or suspended at the time of administration using sterile water, saline, or other appropriate sterile injectable medium.

The antifungal agent and a compound of formula I and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In another aspect, there is provided an antifungal composition comprising an antifungal agent and a compound of formula I:—

[Formula I]

wherein $R^1$ is selected from a nitrile group, an alkyl, alkenyl, amine with 1 to 4 C-atoms that is optionally mono- or polysubstituted by F, O, $NH_2$ or CN, and in which one or more non-adjacent $CH_2$ groups are optionally replaced, in each case independently from one another, by —O—, —NH—, —CO—, —COO—, or —OCO—;

$R^2$ is hydrogen or a hydroxy or alkoxy group with 1 to 3 C atoms;

$R^3$ is a straight chain or branched alkyl or alkylene with 4 to 20 C atoms, that is optionally mono- or polysubstituted by a $C_1$ to $C_4$ alkyl group;

$R^4$ is hydrogen or a hydroxy or alkoxy group with 1 to 3 C atoms;

$R^5$ is a halogen group; and $R^6$ is H or a $C_1$ to $C_4$ alkyl group;

with the proviso that at least one of $R^2$ and $R^4$ is a hydroxy or alkoxy group with 1 to 3 C atoms.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Embodiments of the invention will now be further described, by way of example only, with reference to the following Examples, and the accompanying drawings in which:—

EXAMPLES

The inventors tested the antifungal activity of a series of novel formulations comprising the compounds described in WO 2013/160670 in combination with a number of different fungicides. WO 2013/160670 discloses Colletochlorin B, which has been shown to be an inhibitor of microbial alternative oxidase (AOX) and/or cytochrome $bc_1$ complex.

Example 1—Assays Used to Test Fungicides Against Fungi (e.g. *Chalara fraxinea*)

Figure 7:
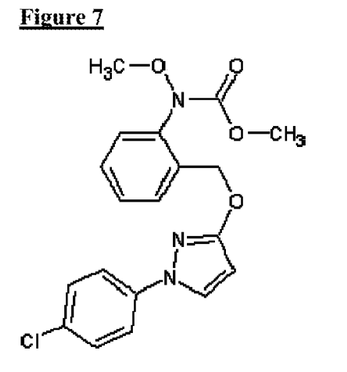
FIG. 7 represents the chemical formula of Pyraclostrobin.

Materials:
YPD Media/Agar
  2% Yeast extract
  2% Peptone
  2% D-glucose
  2% agar
YPG
  2% Yeast extract
  2% Peptone
  2% Glycerol
  2% agar
Fungicide Formulations Colletochlorin B was synthesised using the methodology described in WO 2013/160670 with reference to FIG. 7. Then, 1 µM of Colletochlorin B is separately combined with 5 M of each of the following fungicides to produce seven different formulations:—
  1) Metalaxyl—belongs to the phenylamide fungicide family (Sukul, P. and M. Spiteller (2000) "Metalaxyl: persistence, degradation, metabolism, and analytical methods." Rev Environ Contam Toxicol 164: 1-26);
  2) Azoxystrobin—belongs to the strobilurin family;
  3) DMI (DeMethylation Inhibitor);
  4) CuPC33—A copper based compound;
  5) Boscalid;
  6) Difenconcozole; and
  7) Pyraclostrobin.
Methods
  1. Yeast strains are streaked out and grown on YPD agar plates for 3 days at 30° C.
  2. 5 mL of YPD liquid media is inoculated with a fungal strain of interest (e.g. *Chalara fraxinea*) and grown for 3 days at 30° C. with shaking at 180 rpm.
  3. 1 µL inoculum of the fungal strain is added to 9999 µL YPG liquid media and gently mixed.
  4. 5 µL of each strain (yeast and fungus) is then plated out on YPG agar plates containing a range of different inhibitor concentrations, for example 1 µM, 1.5 µM and 2 µM of each of the seven formulations comprising 1 µM Colletochlorin B and 5 µM fungicide.
  5. Plates are grown for 3-5 days at 30° C.
  6. The degree of inhibition of fungal/yeast growth caused by the inhibitors is then assessed.
Results The inventors were surprised to observe that for each of the seven combined formulations, a synergistic inhibition effect is seen. For example, the inventors tested Colletochlorin B and Azoxystrobin individually, and in combination, against *Chalara fraxinea*. When the compounds are used separately, partial growth inhibition of the fungus is observed. However, when used in combination, total inhibition is seen. Accordingly, the inventors believe that the seven formulations comprising compound I (preferably, Colletochlorin B) and the various other antifungal compounds can be effectively used to treat or prevent fungal infections.

Example 2—Synergistic Effect of Colletochlorin B and Azoxystrobin Against Fungi (e.g. *S. cerevisiae*)

The inventors tested the efficacy of a combination of Colletochlorin B and azoxystrobin on the growth of *S. cerevisiae*. As in Example 1, Colletochlorin B was synthesised using the methodology described in WO 2013/160670 with reference to FIG. 7.
Methods
  1. *S. cerevisiae* was streaked out and grown up on YPD agar plates for 3 days at 30° C.
  2. 5 mL of YPG liquid media was inoculated with *S. cerevisiae* from the YPD plates and grown for 3 days at 30° C. with shaking at 180 rpm to produce a cell culture.
  3. Approximately $5 \times 10^5$ cells of the *S. cerevisiae* were then plated out onto YPG agar plates containing 1 µM Colletochlorin B, or 1 µM azoxystrobin, or a combination of 1 µM Colletochlorin and 1 µM azoxystrobin.
  4. The plates were incubated for 3-5 days at 30° C.
  5. The degree of inhibition of fungal/yeast growth caused by the inhibitors was then assessed.

Figure 8:
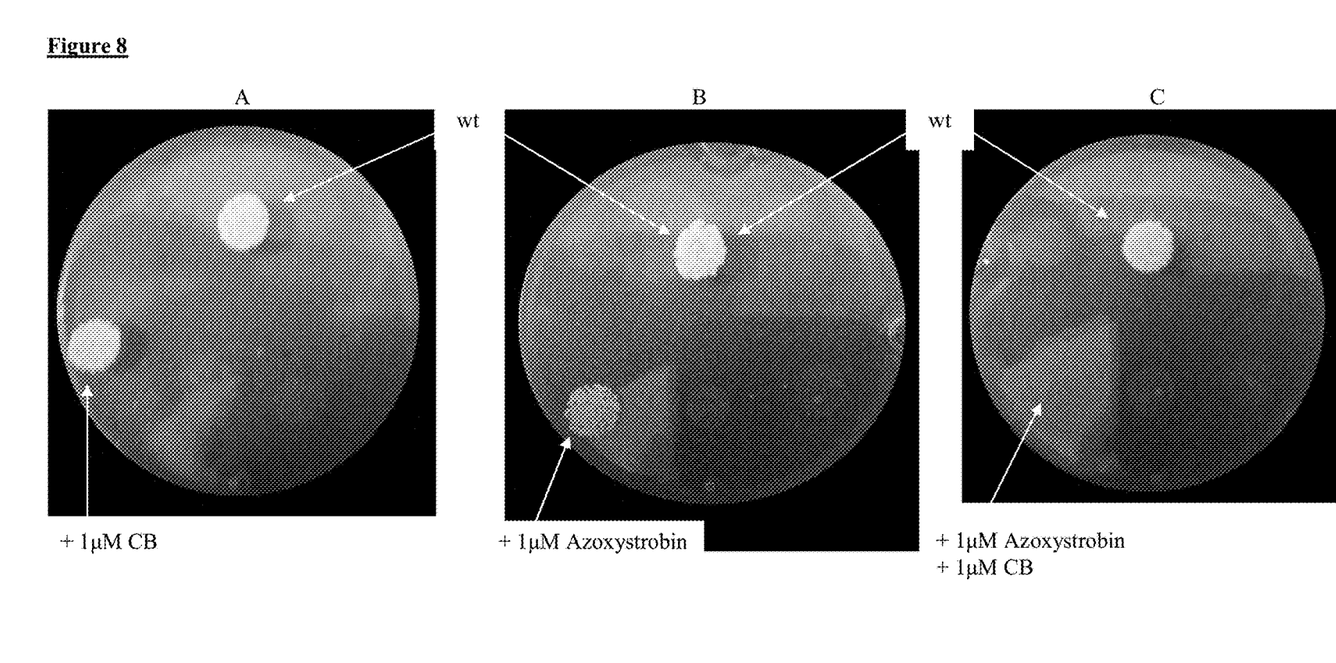
FIG. 8 shows the synergistic effects of Colletochlorin B (1 μM) and Azoxystrobin (1 μM) on the growth S. cerevisiae fungus grown on agar plates.

The plates are shown in FIG. 8. For each plate, the yeast colony grown in the centre at the top was not grown in the presence of any inhibitor acting as a negative control. However, for the plate shown in FIG. 8A, the colony shown on the lower left was grown in the presence of only 1 µM Colletochlorin B, and for the plate shown in FIG. 8B, the colony shown on the lower left was grown in the presence of only 1 µM azoxystrobin. However, for FIG. 8C, the colony on the lower left of the plate was grown in the presence of a combination of 1 µM of azoxystrobin and 1 µM of Colletochlorin B.
Results The inventors tested Colletochlorin B and Azoxystrobin individually (FIGS. 8*a* and 8*b*), and in combination (FIG. 8*c*), against *S. cerevisiae*. When the compounds were used separately, partial growth inhibition of the fungus was observed. However, when used in combination, total inhibition was observed. Accordingly, the inventors have surprisingly demonstrated that a formulation comprising an AOX inhibitor and a conventional fungicide can be effectively used to treat or prevent fungal infections.

The invention claimed is:
1. An antifungal composition comprising an antifungal agent and a compound of formula I:—

[Formula I]

wherein $R^1$ is CHO or CN;
  $R^2$ is a hydroxyl group;
  $R^3$ is a branched alkylene with 4 to 12 C atoms;
  $R^4$ is a hydroxyl group;

$R^5$ is a halogen group; and
$R^6$ is a methyl group;
wherein the antifungal agent is Azoxystrobin, and the compound of formula I can synergize with the Azoxystrobin to treat a fungal infection.

2. An antifungal composition according to claim 1, wherein $R^3$ is a branched alkylene with 6 to 12 C atoms.

3. An antifungal composition according to claim 1, wherein $R^5$ is a chlorine or a bromine group.

4. An antifungal composition according to claim 1, wherein:—
$R^1$ is CHO or CN;
$R^2$ is a hydroxyl group;
$R^3$ is an alkylene chain having 8 to 10 C atoms, and is substituted with at least one methyl group;
$R^4$ is a hydroxyl group;
$R^5$ is a chlorine or bromine atom; and
$R^6$ is a methyl group.

5. An antifungal composition according to claim 1, wherein:—
$R^1$ is CHO or CN;
$R^2$ is a hydroxyl group;
$R^3$ is an alkylene chain having 8 to 10 C atoms, and is substituted with two methyl groups;
$R^4$ is a hydroxyl group;
$R^5$ is a chlorine atom; and
$R^6$ is methyl group.

6. An antifungal composition according to claim 1, wherein:—
$R^1$ is CHO;
$R^2$ is a hydroxyl group;
$R^3$ is an alkylene chain having 8 to 10 C atoms, and is substituted with two methyl groups;
$R^4$ is a hydroxyl group;
$R^5$ is a chlorine atom; and
$R^6$ is a methyl group.

7. An antifungal composition according to claim 1, wherein:—
$R^1$ is CHO;
$R^2$ is a hydroxyl group;
$R^3$ is a diene having 8 to 10 C atoms, and is substituted with two methyl groups;
$R^4$ is a hydroxyl group;
$R^5$ is a chlorine atom; and
$R^6$ is a methyl group.

8. An antifungal composition according to claim 1, wherein the compound of formula I is Colletochlorin B.

9. An antifungal composition according to claim 1, wherein $R^3$ is

10. An agrochemical composition comprising the antifungal composition according to claim 1.

11. A method of treating, ameliorating or preventing an agrochemical disease or infection in a plant, the method comprising contacting a plant in need of such treatment with an agrochemically effective amount of the anti-fungal composition of claim 1.

12. The method according to claim 11, wherein the disease or infection is caused by an organism selected from a group consisting of: *Chalara fraxinea*; *Septoria tritici*; *Gaeumannomyces gramminis var titici*; *Magnaporthe grisea*; *Magnaporthe oryzae*; *Rhizoctonia solani*; *Botrytis cinerea*; *Fusicladium effusum* syn. *Cladosporium caryigenum* and *Fusicladosporium effusum*; *Carya illinoinensis*; *Podosphaera fusca*; *Microdochium nivale*; *Microdochium majus*; *Septoria nodoum*; *Tapesia acuformis*; *Mycosphaerella fijiensis*; *Metarhizium anisopliae*; a filamentous fungus; *Ascomycete*; *Aspergillus*; *Blumeria*; *Candida*; *Cryptococcus*; *Encephalitozoon*; *Fusarium*; *Leptosphaeria*; *Magnaporthe*; *Phytophthora*; *Plasmopara*; *Pneumocystis*; *Pyricularia*; *Pythium*; *Puccinia*; *Rhizoctonia*; *Richophyton*; *Ustilago*; and *Saccharomyces* spp.

13. The method according to claim 11, wherein the disease or infection is caused by yeast.

14. The method of claim 13, wherein the yeast is *Saccharomyces* spp. or *Candida* spp.

* * * * *